(12) United States Patent
Bastide et al.

(10) Patent No.: US 10,671,151 B2
(45) Date of Patent: Jun. 2, 2020

(54) MITIGATING DIGITAL REALITY LEAKAGE THROUGH SESSION MODIFICATION

(71) Applicant: INTERNATIONAL BUSINESS MACHINES CORPORATION, Armonk, NY (US)

(72) Inventors: Paul R. Bastide, Boxford, MA (US); Matthew E. Broomhall, Goffstown, NH (US); Liam S. Harpur, Skerries (IE); Lin Sun, Cary, NC (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 15/685,268

(22) Filed: Aug. 24, 2017

(65) Prior Publication Data
US 2019/0064919 A1    Feb. 28, 2019

(51) Int. Cl.
| | |
|---|---|
| H04N 7/16 | (2011.01) |
| G06F 3/01 | (2006.01) |
| H04L 29/08 | (2006.01) |
| G06T 19/00 | (2011.01) |
| A61B 5/16 | (2006.01) |

(52) U.S. Cl.
CPC .............. G06F 3/011 (2013.01); A61B 5/165 (2013.01); G06T 19/003 (2013.01); H04L 67/22 (2013.01); G06F 2203/011 (2013.01)

(58) Field of Classification Search
CPC ................................. G06F 3/011; G06F 3/013
USPC ....................................................... 725/153
See application file for complete search history.

(56) References Cited

U.S. PATENT DOCUMENTS

| | | |
|---|---|---|
| 6,707,447 B1 | 3/2004 | Goranowski |
| 9,053,654 B2 | 6/2015 | Sherman |
| (Continued) | | |

OTHER PUBLICATIONS

Cohn et al., "Reducing Negative Effects from Virtual Environments: Implications for Just-In-Time Training", Paper presented at the RTO HFM Symposium on "Spatial Disorientation in Military Vehicles: Causes, Consequences and Cures", held in La Coruila, Spain, Apr. 15-17, 2002, and published in RTO-MP-086, Unclassified, Defense Technical Information Center, Compilation Part Notice, ADP013880, pp. 38-1-38-9.

(Continued)

Primary Examiner — Jivka A Rabovianski
(74) Attorney, Agent, or Firm — L. Jeffrey Kelly

(57) ABSTRACT

A method, computer program product, and system for mitigating disorientation of a user transitioning out of a digital reality session. A user login credentials is received. A start digital reality session command is received. User behavior inputs associated with the digital reality session are monitor. In response to analyzing the user behavior inputs, a behavior risk rating associated with the user behavior inputs is generated. An ending event to the digital reality session is detected. A leakage length value based on the generated behavior risk rating is generated. An expected leakage length value based on the analyzed behavior associated with the user and a user profile associated with the user is determined. A leakage risk value based on the behavior risk rating and leakage length value is assigned. In response to the leakage risk value being above a threshold, the digital reality session is modified.

20 Claims, 4 Drawing Sheets

(56) References Cited

U.S. PATENT DOCUMENTS

2015/0310758 A1\* 10/2015 Daddona .................. G09B 9/02
434/62
2018/0046851 A1\* 2/2018 Kienzle .................. G06F 3/017

OTHER PUBLICATIONS

Dirckx, "Hyperbaric Oxygen Therapy", www.hpisum.com, e-Perspectives, Sep. 2009, pp. 21-23.
Greunke, Charlie, "development of a light-weight, virtual reality trainer for the LSO community: time to make the leap toward immersive VR", Calhoun, Institutional Archive of the Naval Postgraduate School, DSpace Repository, Theses and Dissertations, Sep. 2015, Monterey, California: Naval Postgraduate School, http://hdl.handle.net/10945/47267, Downloaded from NPS Archive: Calhoun, 202 pages.
Kanugo, "Blurring the Lines betweenRealworld and VirtualWorld. How Soon?", Aug. 6, 2015, 6 pages.
Miller et al., Treatment of Acute, Adverse Psychedelic Reactions: "I've Tripped and I Can't Get Down", Journal of Psychoactive Drugs, vol. 24, 1992, Issue 3, pp. 277-279.
Pearce et al., "Playing ethnography: a study of emergent behaviour in online games and virtual worlds","Communities of Play: The Social Construction of Identity in Persistent Online Game Worlds", ual: university of the arts London, 2006, 8 pages.
Business Insider, "NextVR promises to blur the lines between the real world and virtual reality", Nov. 22, 2016, 9 pages.
Plunkett, "New running apps blur the line between virtual reality and real life", The Washington Post, Wellness, Jul. 20, 2016, 4 pages.
Hicks, "The blurring line between virtual reality and real life", Virtual Worlds, The week of Jun. 28, 2015, https://kernelmag.dailydot.com/issue-titles/13513/virtual-spaces-issue/, 4pages.

\* cited by examiner

MITIGATING DIGITAL REALITY LEAKAGE THROUGH SESSION MODIFICATION

BACKGROUND

The present invention relates generally to the field of and virtual reality devices, and more particularly to mitigating any negative social effects of exiting an augmented or virtual reality session.

The technical goal of virtual reality ("VR") or augmented reality ("AR") is to replace real sense perceptions by the computer-generated ones derived from a mathematical database describing a 3D scene, animations of objects within the scene, or represented as transformations over sets of mathematical objects, including changes caused by the intervention of the participant. If sensory perceptions are indeed effectively substituted then the brain has no alternative but to infer its perceptual model from its actual stream of sensory data, and consciousness may be transformed to the virtual scenario rather than the real one, in spite of the participant's knowledge that the participant is engaged in a non-real, or digital reality. It may be advantageous to mitigate confusion between this inference that VR or AR is the same as traditional reality ("TR"), or the real world.

SUMMARY

Embodiments of the present invention disclose a method, computer program product, and system for mitigating disorientation of a user transitioning out of a digital reality session. A user login credentials is received. A start digital reality session command is received. User behavior inputs associated with the digital reality session are monitor. In response to analyzing the user behavior inputs, a behavior risk rating associated with the user behavior inputs is generated. An ending event to the digital reality session is detected. A leakage length value based on the generated behavior risk rating is generated. An expected leakage length value based on the analyzed behavior associated with the user and a user profile associated with the user is determined. A leakage risk value based on the behavior risk rating and leakage length value is assigned. In response to the leakage risk value being above a threshold, the digital reality session is modified.

DETAILED DESCRIPTION

Figure 1:
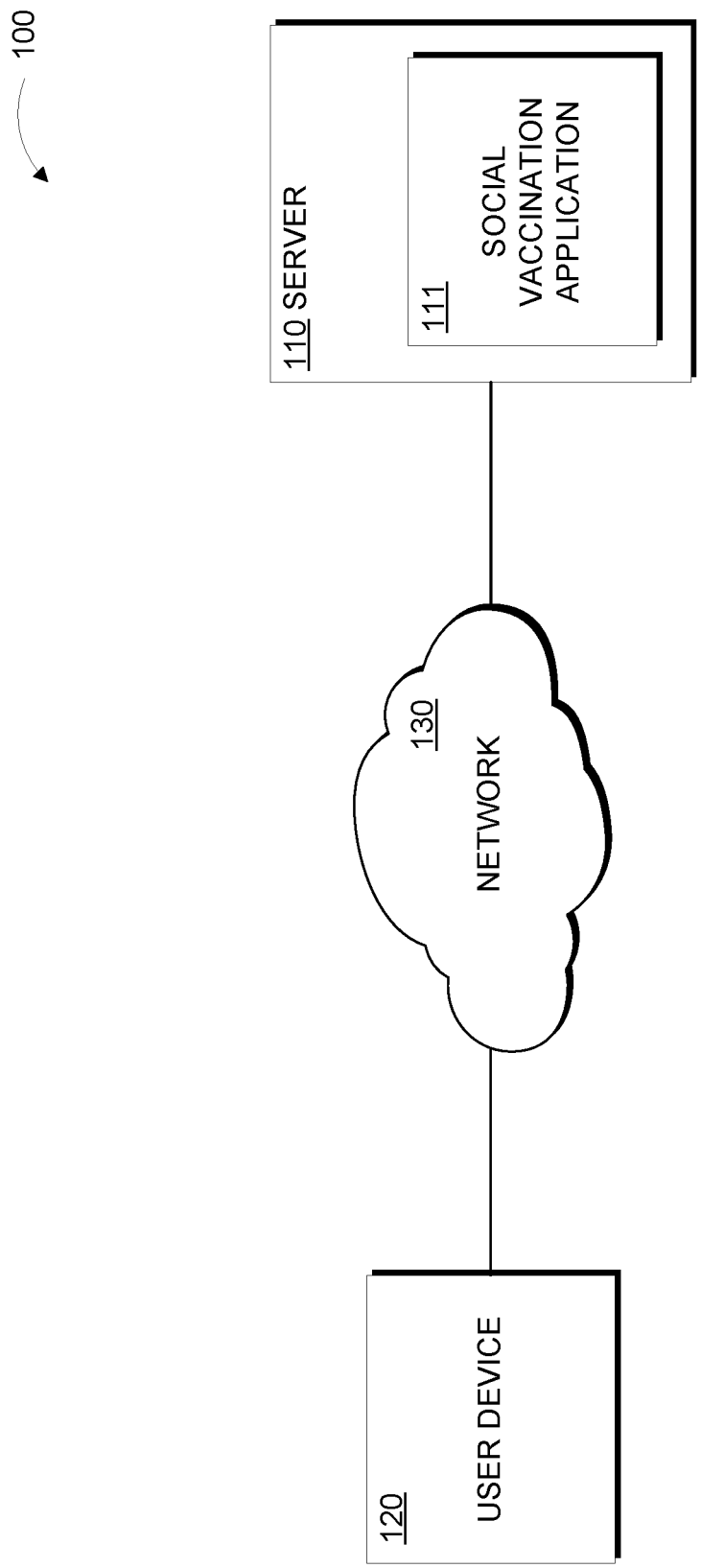
FIG. 1 is a functional block diagram illustrating a distributed data processing environment, in accordance with an embodiment of the present invention.

Detailed embodiments of the claimed structures and methods are disclosed herein; however, it can be understood that the disclosed embodiments are merely illustrative of the claimed structures and methods that may be embodied in various forms. This invention may, however, be embodied in many different forms and should not be construed as limited to the exemplary embodiments set forth herein. Rather, these exemplary embodiments are provided so that this disclosure will be thorough and complete and will fully convey the scope of this invention to those skilled in the art. In the description, details of well-known features and techniques may be omitted to avoid unnecessarily obscuring the presented embodiments.

References in the specification to "one embodiment", "an embodiment", "an example embodiment", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

Many augmented reality or wearable device vendors, such as Oculus Rift™ (Facebook™), Google Glasses™, and Samsung™ Virtual Reality are driving changes in user behavior. Real world, or traditional information, is increasingly being presented in combination with augmented/virtual reality, or digital reality, via, for example, games, overlaying map information, and manipulation of digital objects integrated with traditional reality. Digital reality's combination of live views with digital flags and markers enable information to be presented to a user, and allows user interaction. Improvements in interactions between digital reality and traditional realities may cause the blurring of digital and traditional realities. It should be appreciated that all products and service names are trademarks of their respective owning entities.

Those that engage with digital reality technology may expect more pervasive and instantly interchangeable digital experience and an increase in use of digital reality features. For example, digital realities may be implemented and used to begin a remote video conferencing session while one or more conference participants are commuting to an office and then the conferencing session may transition to traditional realities when the employee(s) have arrived at the office. In this video conferencing example, digital realities may be used in conjunction with other video conferencing technology found in the art, or exclusively as a digital experience. Digital reality can enable a continuous conversation between the remote conference user and an in office user, then stop the digital reality session and have a traditional conversation and interaction commence when the two users are within a geographic proximity with each other. The digital reality session may restart if the distance between users crosses or exceeds a threshold. In this way, a user may engage in digital reality sessions and may do so many times throughout the day. Over prolonged use, a blurring of realities may occur causing some users to experience symptoms such as reality leakage or confusion between digital reality and traditional reality.

Increasingly, when transitioning between digital realities and traditional realities, disorientation between realities can occur and there may also be an excessively adverse experience, which may cause injury, whether physical or social, to the user or. For example, constant interaction with digital realities may cause the misjudgment of the speed of oncoming cars, underestimated reaction times, and subconscious disregard for traditional reality hazards. This subconscious disregard for traditional reality hazards may be considered as digital reality norms subsisting, or leaking, into traditional reality. This subsistence, or digital reality leakage, may cause the digital reality user adverse experiences, therefore, it may be advantageous to mitigate leakage when it occurs and prevent leakage from initially occurring. It should be appreciated that all products and service names are trademarks of their respective owning entities.

Embodiments of the present invention relate to the field of computing, and more particularly to virtual reality, augmented reality, and mixed reality, which may collectively be referred to as digital reality. The following described exemplary embodiments provide a system, method, and program product to, among other things, mitigate disorientation of a user transitioning out of a virtual reality, augmented reality, or mixed reality session. Therefore, the present embodiment has the capacity to improve the technical field of virtual reality, augmented reality and mixed reality by utilizing the virtual reality, augmented reality, or mixed reality device to provide audio and/or visual cues and alerts in response to detected atypical behavior of a user transitioning out of a virtual reality, augmented reality, or mixed reality experience session. It may be advantageous to make sure that the user of virtual reality, augmented reality and mixed reality knows that they have transitioned back into traditional reality or the real world and needs to conform to typical social norms that may be disregarded while using VR and AR devices and applications.

The present invention will now be described in detail with reference to the Figures. FIG. 1 is a functional block diagram illustrating a distributed data processing environment, generally designated 100, in accordance with one embodiment of the present invention.

The distributed data processing environment 100 includes a server 110 and a user device 120, all interconnected over a network 130.

The user device 120 may be any programmable electronic device capable of display where the display is capable of providing a digital reality experience for the user. For example, the user device 120 may include, among other things, a virtual reality headset that provides a virtual reality experience for the wearer. Virtual reality headsets are widely used with computer games but they are also used in other applications, including simulators and trainers. They include a stereoscopic head-mounted display (providing separate images for each eye), stereo sound, and head motion tracking sensors (which may include gyroscopes, accelerometers, structured light systems, etc.). Some virtual reality headsets also have eye tracking sensors and gaming controllers.

The user device 120 may also be an augmented reality device. Augmented reality is a live direct or indirect view of a physical, real-world environment whose elements are augmented by computer-generated sensory input such as sound, video, graphics or GPS data. It is related to a more general concept called computer-mediated reality, in which a view of reality is modified (possibly even diminished rather than augmented) by a computer. Augmented reality enhances one's current perception of reality, whereas in contrast, virtual reality replaces the real world with a simulated one. Augmentation techniques are typically performed in real time and in semantic context with environmental elements, such as overlaying supplemental information like scores over a live video feed of a sporting event. Like above, both virtual reality devices and augmented reality devices may be referred to collectively as digital reality devices for purposes of the following description.

It should be appreciated that user device 120 may be any programmable electronic device capable of conveying real world environments, completely virtual environments, or augmented reality environments.

Server 110 and user device 120 may be a laptop computer, tablet computer, netbook computer, personal computer (PC), a desktop computer, a smart phone, or any programmable electronic device capable of communicating via network, for example, network 130 and with various components and devices within distributed data processing environment 100. Server 110 includes social vaccination application 111. Social vaccination application 111 may communicate with user device 120 and provide an audio or visual overlay to the AUGMENTED REALITY/VIRTUAL REALITY experience of the user. Server 110 and user device 120 may include internal and external hardware components, as depicted and described in further detail with respect to FIG. 4.

Network 130 can be, for example, a local area network (LAN), a wide area network (WAN) such as the Internet, or a combination of the two, and can include wired, wireless, or fiber optic connections. In general, network 130 can be any combination of connections and protocols that will support communications between server 110 and user device 120 along with any other components in distributed data processing environment 100.

In an embodiment, the user device 120 may operate as a digital reality display device while the social vaccination application 111 may run primarily on the server 110. In an alternative embodiment, the social vaccination application 111 may run primarily on the user device 120 while the server 110 may be used for processing and storage of data used by the social vaccination application 111. It should be noted that the social vaccination application 111 may be a standalone program or may be integrated into a larger application.

It should be noted, however, that processing for the social vaccination application 111 may be shared amongst the user device 120 and the server 110 in any ratio. In another embodiment, the social vaccination application 111 may operate on more than one server, user device, or some combination of servers and user devices, for example, a plurality of user devices 120 communicating across the network 130 with a single server 110. In another embodiment, for example, the social vaccination application 111 may operate on a plurality of servers 110 communicating across the network 130 with a plurality of user devices 120. Alternatively, the program may operate on a network server communicating across the network with a server 110 and one or more user devices 120.

In various embodiments of the present invention, social vaccination application 111 may act generally to detect a ending event to a digital reality session. In response to analyzing behavior associated with a user during the detected ending event, social vaccination application 111 may assign a risk rating to the behavior associated with the digital reality activity the user is engaged in. Social vaccination application 111 may determine if leakage will occur and the expected length that the leakage will last. The leakage length may be determined based on an analysis of historical behavior associated with the user and a user profile. Social vaccination application 111 may assign a leakage risk value based on a generated behavior risk rating and expected leakage length (time until exit, time until transition). Social vaccination application 111 may provide feedback to the user within the digital reality session that may mitigate or prevent the user doing negative actions in traditional reality.

In various embodiments, social vaccination application 111 may receive and analyze behavioral data associated with social norms from a predetermined database, corpus, or from aggregated interactions on social media platforms. Social vaccination application 111 may also generate social norms base on the received behavioral data. Specifically, the social vaccination application 111 may compare predetermined base line behavioral data, or social norms, to real time behavioral data received generated by a user digital realty session, or digital session behavior. In an embodiment, the social vaccination application 111 may determine social norms based on an analysis of historical digital session behavior associated with the user. In various embodiments, social vaccination application 111 compares predetermined social norm data to real-time data received by social vaccination application 111 through various sources described above.

In various embodiments, where social norms are unknown for a specific digital reality session, the social vaccination application 111 may determine or measure distances, between the user and objects in traditional reality surroundings. The social vaccination application 111 may generate behavioral guidance for the user, based on the maximum and minimum distances from the user, engaged in a digital reality session, to traditional reality objects and communicate the generated behavioral guidance to the user. In various embodiments, acceptable maximum and minimum distances may change depending on the activity or be predetermined for a particular digital reality session. For example, user input indicating the activity during a digital reality session requires a minimum distance of 3 feet from traditional reality objects. In various embodiments, additional factors social vaccination application 111 may use to determine behavioral guidance include the flexibility of the user (predetermined or based on historical movement data), the average speed of movement of the user at given locations via sensors, accelerometers, global positioning systems ("GPS"), or the like. In various embodiments, social vaccination application 111 may establish distances between objects, or people, in traditional reality surroundings and the user, and determine a distance that does not cross a threshold as distance "norms." Social vaccination application 111 may also integrate cultural norms and enforce those cultural norms based on the user's GPS location.

Figure 2:
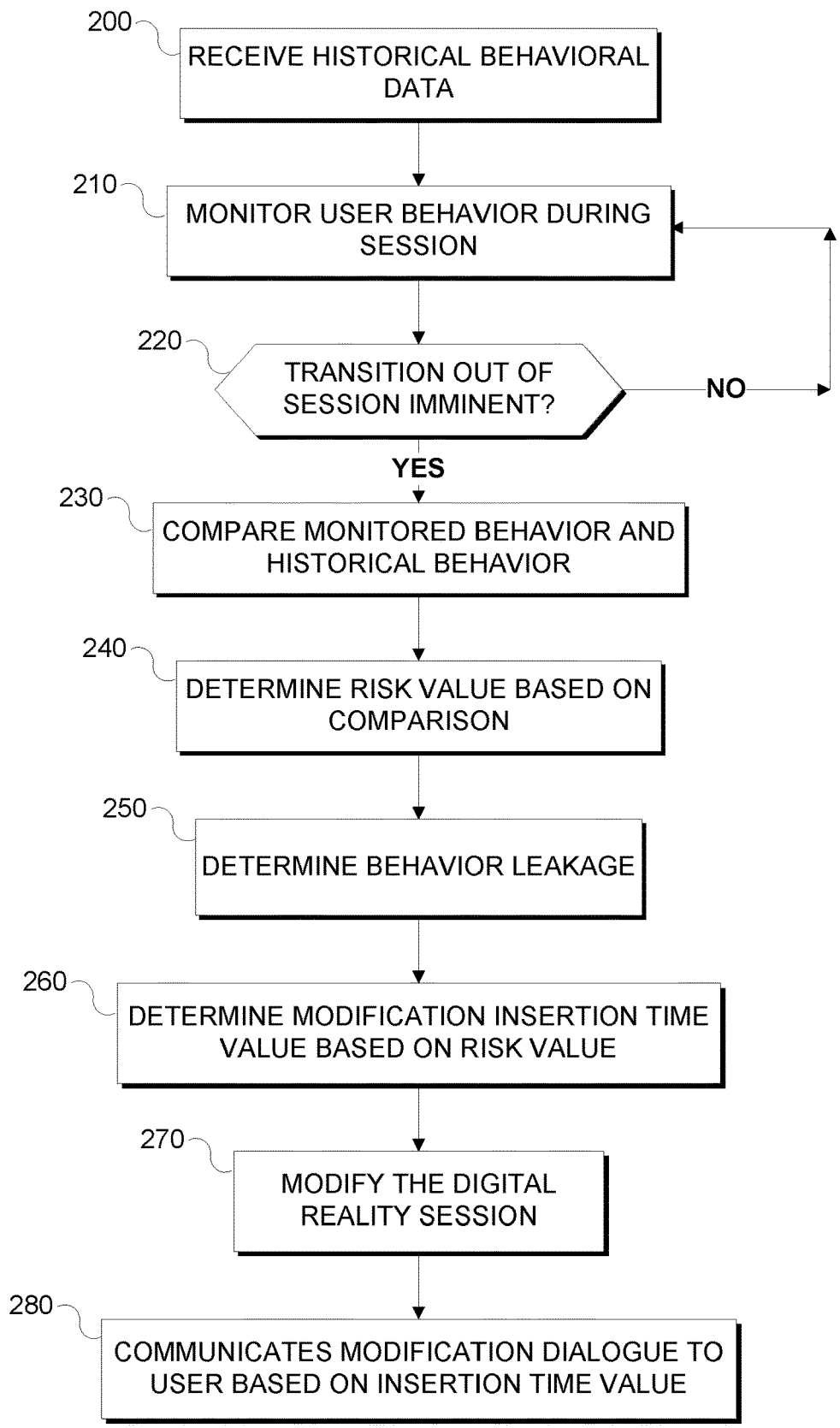
FIG. 2 is a flowchart depicting exemplary operational steps of a social vaccination application, on a server computer within the distributed data processing environment of FIG. 1, in accordance with an embodiment of the present invention.

FIG. 2 is a flowchart depicting exemplary operational steps of social vaccination application 111, on server 110 within distributed data processing environment 100, of FIG. 1, in accordance with an embodiment of the present invention. The social vaccination application 111 may begin by receiving historical behavioral data (block 200). The historical behavioral data may be in a predetermined behavioral corpus stored on a data store, for example, on storage media of server 110, described in further detail below. In various embodiments, the historical behavioral data may be in any database, server, or data storage medium that is capable of communication with server 110 via network 130. The historical behavioral data corpus may contain social behavior statistics related to various activities that take place in the real world that conform to social norms. For example, social norms for driving a car may include speed limits and associated geographical locations. The historical behavioral data corpus may also contain statistics on behavior outside social norms, for example, reckless driving being a behavior outside social norms and the percentage values associated with the rate of reckless driving that occurred within a certain time frame within a certain geographical area.

Social vaccination application 111 further monitors behavioral data generated by a user during a digital reality session (block 210). The social vaccination application 111 may receive a set of tactile data, a set of geographical data associated with the user, social media metadata associated with the user, or a set of physiological sensor data, from the user device 120 during a digital reality session.

The set of tactile data may include body position data measured by various sensors of the user device 120. In addition, the set of tactile data may also be measured by sensors not physically associated with the user device 120, but in communication with the user device 120, for example, remote sensors monitoring user movement and position within a room or confined geographical location. The set of geographical data may include data received from a Global Positioning System (GPS) on the user device 120 or on another device associated with the user's location. The set of social media metadata may include data associated with login credentials associated with the user or a user profile. In various embodiments, the set of social media metadata may be data-mined from one or more social media websites. The set of physiological sensor data may include, for example: heart rate, perspiration rate, blood oxygen levels, blood pressure, blood chemical composition, or the like. In some instances, the physiological sensor data may include only physiological measurements above or below a predetermined threshold.

Additionally, the social vaccination application 111 determines if the user is transitioning out of a digital reality session (block 220). The transition or ending event may be determined based on historical data associated with the user, for example, the last 5 digital reality cycling sessions associated with the user completed at a distance marker of 5-miles, therefore a transition may be imminent as the user crosses a distance marker of 4.5 miles within the session. Ending events may also include words, phrases, or actions taken by the user that, through training and machine learning, social vaccination application 111 may recognize as historically having a high likelihood of indicating a transition out of the digital reality session. For example, if the user is engaged in an exercise digital reality session with a digital trainer, the social vaccination application 111 may receive audio data associated with the user communicating fatigue to the digital trainer. These fatigue words or phrases, for example, may indicate an imminent transition or end of the digital training session. In various embodiments, user device 120 may have a microphone or other means of receiving audio data, as well as other inputs from a user during a digital reality session, communicate the audio data, or other inputs, to the social vaccination application 111, and the social vaccination application 111 may use the received audio data or other inputs as training data.

In various embodiments, ending events may also be triggered by determining a behavior, of the monitored behaviors, in block 210, crosses a threshold that indicates abnormal behavior. For example, an unexpected tactile interaction, unexpected body position, anxiety determined through the physiological sensors, or other physical factor(s). If the user, for example, is engaged in a digital reality cycling session and places both arms in a downward angle not associated with handle bar placement, social vaccination application 111 may determine the digital reality cycling session is coming to an end imminently. However, social vaccination application 111 may determine that the downward angle is associated with resting and indicates the session will continue, depending on the behavior history associated with the user.

In various embodiments, ending events may also be triggered by one or more markers associated with the ending event. These markers may include a length of session value, a likely ending event, an ending activity associated with the user profile history, or a user input associated with a digital reality session end command. A length of session value may be determined based on the length a user engages in a digital reality session. A history of digital reality session lengths may be analyzed. If a user is engaged in a digital reality session approaching a time value associated with past ending time period of previous digital reality sessions, social vaccination application 111 may determine an ending event. A likely ending event may be, for example, a behavior that indicates the end of a session must occur. For example, if a user is ignoring a proximity alert and bumps into a wall, the session may end automatically. Social vaccination application 111 may detect the proximity alert as a likely ending event.

After determining a transition is imminent by comparing the user's behavior during the digital reality session with received historical data (block 220), social vaccination application 111 determines a risk value of the behavior of the user (block 240). The behavior risk value may be determined based on danger associated with the behavior, for example, death or injury associated with sky diving verses attending a picnic. Predetermined danger values may be associated with different behaviors or social vaccination application 111 may determine danger values associated with different behaviors based on reported injury or death of users during various activities.

Social vaccination application 111 determines the potential behavior leakage risk (block 250). As described previously, behavior leakage risk is the likelihood of a user continuing a certain behavior in traditional reality after being engaged in that behavior during a digital reality session. The leakage risk may depend on the engaged digital session behavior and the predicted behavior of the user after transitioning out of the digital reality session. For example, a user A is sitting in a chair at home in a fully simulated virtual reality session engaging in downhill bicycling. User A may be using a hand-held controller as a user input device. The virtual reality simulation, engaged by user A, may have an "all-audience" rating from a gaming regulation authority. User B may be in a fully simulated virtual reality session engaged in a roll playing game where user B is a hero sword fighting an enemy. User B may be using a foam sword that is being tracked by user B's virtual reality device, where the virtual reality device is integrating the movements of the foam sword, in real time, into the simulation. The virtual reality simulation, engaged by user B, may have a "mature" rating from a gaming regulation authority. Social vaccination application 111 may determine that user A has a lower leakage risk than user B based on the simulation rating, the nature of the simulation, and the user input device used. For example, without mitigation or modification of the simulation at the exit time, user B may continue swinging the sword, with the potential for damaging property.

In another example, User C, located in the United States may be engaged in an augmented reality session where use C is viewing a traditional reality paints, canvas, and easel with an augmented reality overlay of a simulated art studio in France, with various simulated landmark viewable through simulated windows. User D may be engaged in an augmented reality session using a traditional reality bicycle with an augmented reality overlay of obstacles and goals, with the game objective of avoiding simulated obstacles and riding through simulated goals. Social vaccination application 111 may determine that user C will have a lower leakage risk than user D. Social vaccination application 111 may determine that the risk of user C confusing their location after the end of the augmented reality session may be lower than the risk of user D engaging in high speed maneuvers, for simulated points, even after the end of the augmented reality session. Social vaccination application may apply a leakage risk value of 5.0 to user D's behavior and a leakage risk value of 0.8 to user C's behavior.

The digital reality session may be modified to prevent unwanted behavior from leaking and becoming actions taken in traditional reality. After determining the leakage risk value, the social vaccination application 111 determines a modification insertion time value (block 260). The modification insertion time value is the time during the digital reality session at which a modification, or alteration to the digital reality session, is conveyed to the user. The modification insertion time value may be conveyed to the user, by any means, for example, displayed text or an audio alter. In various embodiments, the insertion time is a time period before the user discontinues the digital reality session that the modification will need to be implemented in order to prevent behavioral leakage. For example, user A engaged in a virtual reality downhill bicycling session, discussed above, may only need a modification of the virtual reality session 1 second before transitioning to traditional reality. User B engaged in the virtual reality roll playing game session may need modifications to the virtual reality session 5 minutes before transitioning to traditional reality. In various embodiments, social vaccination application 111 may base the modification insertion time value on the leakage risk, where a higher leakage corresponds to a longer modification insertion time value.

Social vaccination application 111 modifies the digital reality session (block 270) based on the monitored behavior, historical behavior, determined risk value, determined behavior leakage, and leakage length value (blocks 230-260) Modification of the digital reality session may include a dialogue, for example, generating a text message for display, an audio prompt, visual data for display, or a hyperlink, overlaid on the digital reality session. Dialogues may be predetermined such that a particular dialogue is associated with a certain behavior, or social vaccination application 111 may generate unique dialogues based on the user profile history, received linguistic data associated with the user profile, or social media metadata associated with the user profile.

In various embodiments, the social vaccination application 111 communicates the generated modification to the digital reality session to the user, for example, to user device 120 via server 110 (block 280). In various embodiments, social vaccination application 111 may monitor behavior associated with downhill cycling, in which the digital reality session simulates high speeds, dodging traffic and hitting obstacles with no consequence, for example, a collision only restarts the lap/session. For example, in various embodiments, after detecting a ending event, and determining the behavior engaged by the user in the digital reality session is high risk, and leakage likely, social vaccination application 111 may generate a hyperlink to a video on cycling safety, display a message to slow down and stay on the road, and/or generate and communicate audio that the user is ending the digital reality session and they must now "follow the rules of the road".

Figure 3:
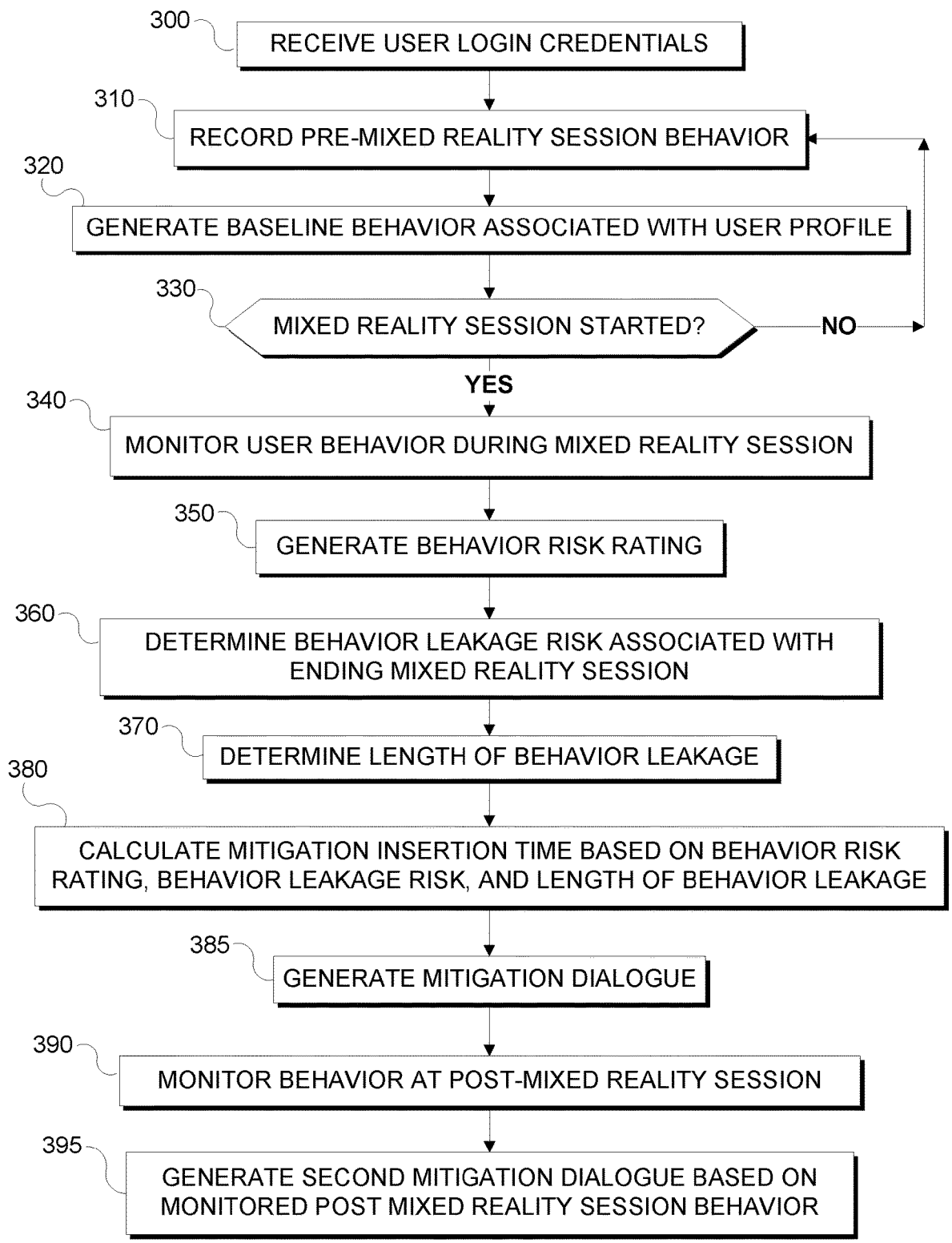
FIG. 3 is a flowchart depicting alternative exemplary operational steps of a social vaccination application, on a server computer within the distributed data processing environment of FIG. 1, in accordance with an embodiment of the present invention.

FIG. 3 is a flowchart depicting exemplary operational steps of the social vaccination application 111, on server 110 within the distributed data processing environment 100, in accordance with an alternative embodiment of the present invention. In various embodiments, social vaccination application 111 receives user login credentials (block 300) and generates a user profile based on the received credentials. A user may set up a user profile and make selections from a graphical user interface (GUI), for example, via a web browser. In various embodiments, the user profile links with social media accounts associated with the received login credentials such that social vaccination application 111 is able to utilize datamining and analyze social media data or social media metadata using any tools know in the art, for example, Natural Language Processing. In various embodiments, social vaccination application 111 may generate a behavior history based on the received social media metadata.

In various embodiments the digital reality device, for example, user device 120, is a wearable device that a user will have on continuously and social vaccination application 111 records, and stores in a data store, the user behavior prior to the user engaging in any digital reality sessions (block 310). Social vaccination application 111 generates a baseline behavior history associated with the user (block 320) based on the recorded pre-session behavior and datamined social media metadata.

Social vaccination application 111 detects the start of a digital reality session (block 330) and monitors the user's behavior during the digital reality session (block 340). In various embodiments, social vaccination application 111 starts a digital reality session, in response to receiving a start digital reality session command. In various embodiments, social vaccination application 111 determines the start of a digital reality session based on social media metadata, GPS data, and a received set of tactile data. The tactile data may be based on the user's interaction with the user device, for example user device 120, a set of body position data and a set of physiological sensor data. In various embodiments, social vaccination application 111 determines the start of a digital reality session based on the received data being above a predetermined threshold indicating the start of a digital reality session.

Social vaccination application 111 generates a behavior risk rating (block 350) as described above. Social vaccination application 111 determines a behavior leakage risk associated with the ending of the digital reality session (block 360). Social vaccination application 111 determines the potential length of the leakage, or leakage length value (block 370) where the leakage length value is the potential time the user would engage in similar activity as in the digital reality session without mitigation. In various embodiments, social vaccination application 111 generates the behavior risk rating, determines the behavior leakage risk, and determines the leakage length value based on the received social media metadata associated with the user login credentials. Leveraging the social media metadata may allow social vaccination application 111 determine leakage values more efficiently.

In various embodiments, social vaccination application 111 calculates the mitigation insertion time (block 380) based on the determined behavioral risk rating, behavior leakage risk, and length of behavior leakage value. Social vaccination application 111 may generate mitigation dialogue for display (block 385) based on the user profile and behavioral history associated with the user. In various embodiments, social vaccination application 111 may generate mitigation dialogue based on the received social media metadata. Utilizing the received social media metadata may enable social vaccination application 111 to replicate the style, language, tone, or the like, of a user's social media profile. This may enable social vaccination application 111 to minimize the leakage, as a user receiving dialogue based on social media data may be more receptive to the generated dialogue.

In various embodiments, social vaccination application 111 periodically monitors the behavior of the user after the transition (block 390). Monitoring of the user's behavior after the user exits the digital reality session may be necessary to determine if leakage has occurred. Social vaccination application 111 may compare the user's behavior after exiting the digital reality session with behavior associated with the digital reality. If the behavior comparison crosses a threshold, session social vaccination application 111 generates additional mitigation dialogue to communicate to the user (block 395) via, for example, user device 120, social media notification, mobile push notification, or any other electronic device capable of communication with social vaccination application 111 via server 110.

Figure 4:
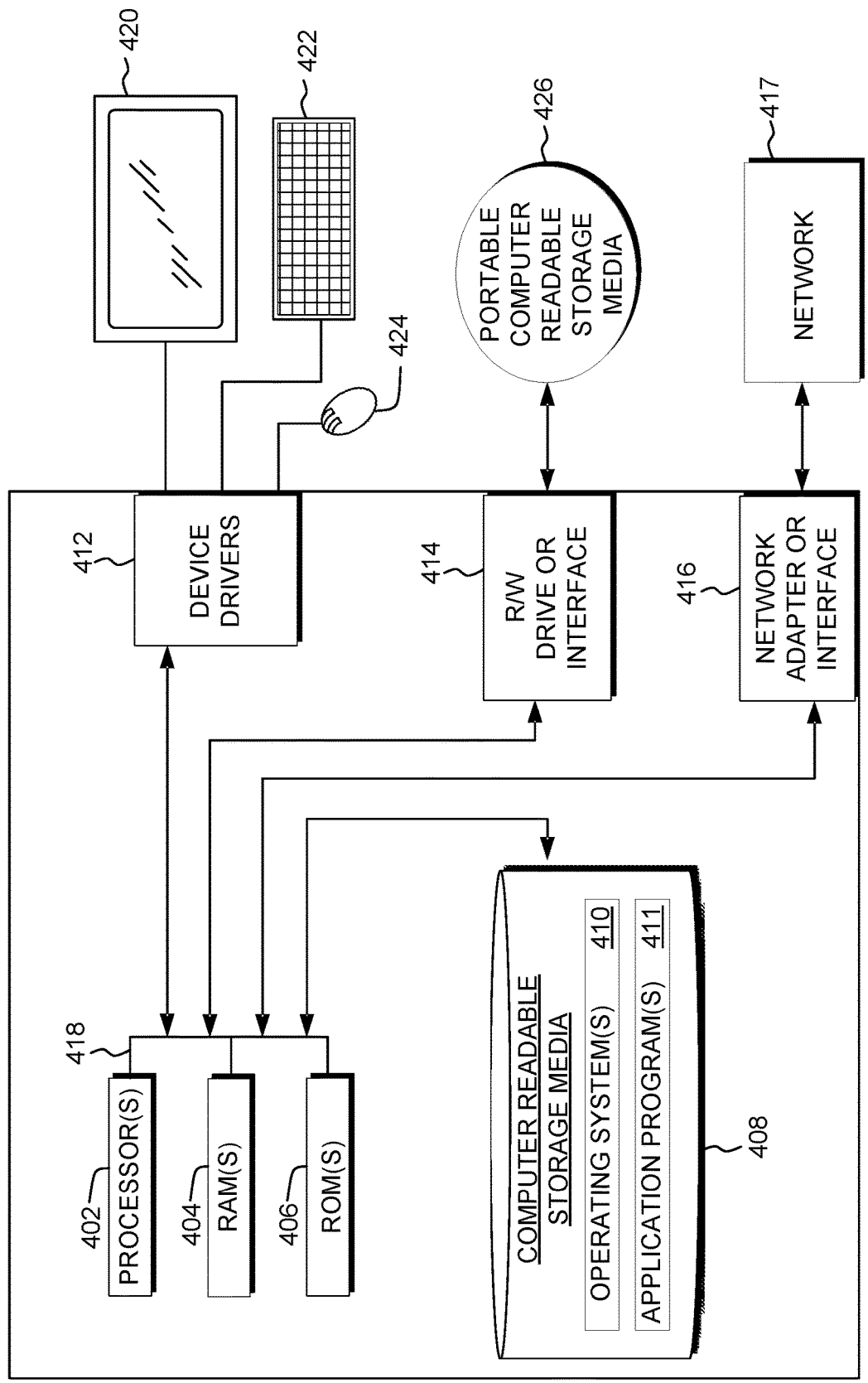
FIG. 4 depicts a block diagram of components of the server computer executing the ingestion application, in accordance with an embodiment of the present invention.

FIG. 4 depicts a block diagram of components of server 110 of the distributed data processing environment 100 of FIG. 1, in accordance with an embodiment of the present invention. It should be appreciated that FIG. 4 provides only an illustration of one implementation and does not imply any limitations with regard to the environments in which different embodiments may be implemented. Many modifications to the depicted environment may be made.

Server 110 may include one or more processors 402, one or more computer-readable RAMs 404, one or more computer-readable ROMs 406, one or more computer readable storage media 408, device drivers 412, read/write drive or interface 414, network adapter or interface 416, all interconnected over a communications fabric 418. Communications fabric 418 may be implemented with any architecture designed for passing data and/or control information between processors (such as microprocessors, communications and network processors, etc.), system memory, peripheral devices, and any other hardware components within a system.

One or more operating systems 410, and one or more application programs 411, for example, social vaccination application 111, are stored on one or more of the computer readable storage media 408 for execution by one or more of the processors 402 via one or more of the respective RAMs 404 (which typically include cache memory). In the illustrated embodiment, each of the computer readable storage media 408 may be a magnetic disk storage device of an internal hard drive, CD-ROM, DVD, memory stick, magnetic tape, magnetic disk, optical disk, a semiconductor storage device such as RAM, ROM, EPROM, flash memory or any other computer-readable tangible storage device that can store a computer program and digital information.

Server 110 may also include an R/W drive or interface 414 to read from and write to one or more portable computer readable storage media 426. Application programs 411 on server 110 may be stored on one or more of the portable computer readable storage media 426, read via the respective R/W drive or interface 414 and loaded into the respective computer readable storage media 408.

Server 110 may also include a network adapter or interface 416, such as a TCP/IP adapter card or wireless communication adapter (such as a 4G wireless communication adapter using OFDMA technology) for connection to a network 428. Application programs 411 on server 110 may be downloaded to the computing device from an external computer or external storage device via a network (for example, the Internet, a local area network or other wide area network or wireless network) and network adapter or interface 416. From the network adapter or interface 416, the programs may be loaded onto computer readable storage media 408. The network may comprise copper wires, optical fibers, wireless transmission, routers, firewalls, switches, gateway computers and/or edge servers.

Server 110 may also include a display screen 420, a keyboard or keypad 422, and a computer mouse or touchpad 424. Device drivers 412 interface to display screen 420 for imaging, to keyboard or keypad 422, to computer mouse or touchpad 424, and/or to display screen 420 for pressure sensing of alphanumeric character entry and user selections. The device drivers 412, R/W drive or interface 414 and network adapter or interface 416 may comprise hardware and software (stored on computer readable storage media 408 and/or ROM 406).

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The programs described herein are identified based upon the application for which they are implemented in a specific embodiment of the invention. However, it should be appreciated that any particular program nomenclature herein is used merely for convenience, and thus the invention should not be limited to use solely in any specific application identified and/or implied by such nomenclature.

Based on the foregoing, a computer system, method, and computer program product have been disclosed. However, numerous modifications and substitutions can be made without deviating from the scope of the present invention. Therefore, the present invention has been disclosed by way of example and not limitation.

What is claimed is:

1. A method for mitigating disorientation of a user transitioning from a digital reality session to traditional reality, comprising:
    receiving historical behavioral data comprising social behavior statistics related to activities in traditional reality that conform to social norms and social behavior statistics related to activities in traditional reality that do not conform to social norms;
    monitoring behavioral data generated by a user during the digital reality session;
    detecting an ending event to the digital reality session indicating the user is transitioning from the digital reality session to traditional reality by comparing the received historical behavioral data and the monitored behavioral data;
    determining a risk value of the behavior of the user based on a danger associated with the user's behavior;
    determining a behavior leakage risk associated with the ending event, wherein the behavior leakage risk is the likelihood of the user continuing a certain behavior in traditional reality after being engaged in that behavior during the digital reality session, the behavior leakage risk depends on the user's behavior during the digital reality session and predicted behavior of the user after transitioning out of the digital reality session; and
    determining a modification insertion time, the modification insertion time is a time period before the user discontinues the digital reality session that a modification to the digital reality session will need to be implemented in order to prevent behavioral leakage; and
    modifying the digital reality session to prevent unwanted behavior from leaking and becoming actions taken by the user in traditional reality, the modification is based on the received historical behavioral data, the monitored behavioral data, the determined risk value, the determined behavior leakage risk, and the modification insertion time.

2. The method of claim 1, wherein the ending event is based on one or more of:
    a previous ending event based on a user profile history associated with the user;
    one or more markers associated with the previous ending event; and
    an ending event likelihood value associated with the behavior crossing a threshold value.

3. The method of claim 1, wherein the ending event is based on one or more markers associated with a previous ending event, the one or more markers comprising one or more of:
    a length of session value determined based on the length the user engages in a prior digital reality session;
    a likely ending event including a behavior that indicates the end of a particular digital reality session must occur;
    an ending activity associated with a user profile history associated with the user; and
    a user input associated with a digital reality session end command.

4. The method of claim 1, wherein monitoring the behavioral data generated by the user during the digital reality session comprises one or more of:
    receiving a set of tactile data based on the user interaction with a user device;
    receiving a set of body position data;
    receiving geographical data associated with the user;
    receiving social media data associated with the user; and
    receiving a set of physiological sensor data associated with the user and above a predetermined threshold value.

5. The method of claim 1, wherein determining the risk value of the behavior of the user comprises:
    determining a baseline behavior rating based on the user login credentials;
    calculating a behavior rating based on real time behavior data of a user during the digital reality session; and
    comparing the baseline behavior rating and the calculated behavior rating.

6. The method of claim 1, wherein modifying the digital reality session to prevent unwanted behavior from leaking and becoming actions taken by the user in traditional reality comprises one or more of:
    generating a text dialogue for display;
    generating an audio prompt associated with the generated dialogue for display;
    generating visual data for display; and
    communicating a hyperlink for display to the user device.

7. The method of claim 1, wherein the behavior leakage risk is further based on the nature of a simulation carried out during the digital reality session and a user input device required to carry out that simulation.

8. A method for mitigating disorientation of a user transitioning from a digital reality session to traditional reality, comprising:
    receiving historical behavioral data comprising social behavior statistics related to activities in traditional reality that conform to social norms and social behavior statistics related to activities in traditional reality that do not conform to social norms;
    monitoring behavioral data generated by a user during the digital reality session;
    detecting an ending event to the digital reality session indicating the user is transitioning from the digital reality session to traditional reality by comparing the received historical behavioral data and the monitored behavioral data to determine;

determining a risk value of the behavior of the user based on a danger associated with the user's behavior;

determining a behavior leakage risk associated with the ending event based on the nature of the simulation carried out during the digital reality session and the user input device required to participate in the digital reality session, the behavior leakage risk is the likelihood of the user continuing a certain behavior in traditional reality after being engaged in that behavior in the digital reality session;

determining a modification insertion time, the modification insertion time is a time period before the user discontinues the digital reality session that a modification to the digital reality session will need to be implemented in order to prevent behavioral leakage; and modifying the digital reality session to prevent unwanted behavior from leaking and becoming actions taken by the user in traditional reality, the modification is based on the received historical data, the monitored behavioral data, the determined risk value, the determined behavior leakage risk, and the determined modification insertion time, wherein modifying the digital reality session comprises:
generating a text dialogue and associated audio prompt for communication to the user during the digital reality session;
generating visual data for communication to the user during the digital reality session; and
generating a hyperlink accessible by the user during the digital reality session.

9. The method of claim 8, wherein the ending event is based on one or more of:
a previous ending event based on a user profile history associated with the user;
one or more markers associated with the previous ending event; and
an ending event likelihood value associated with the behavior crossing a threshold value.

10. The method of claim 8, wherein the ending event is based on one or more markers associated with a previous ending event, the one or more markers comprising one or more of:
a length of session value determined based on the length the user engages in a prior digital reality session;
a likely ending event including a behavior that indicates the end of a particular digital reality session must occur;
an ending activity associated with a user profile history associated with the user; and
a user input associated with a digital reality session end command.

11. The method of claim 8, wherein monitoring the behavioral data generated by the user during the digital reality session comprises one or more of:
receiving a set of tactile data based on the user interaction with a user device;
receiving a set of body position data;
receiving geographical data associated with the user;
receiving social media data associated with the user; and
receiving a set of physiological sensor data associated with the user and above a predetermined threshold value.

12. The method of claim 8, wherein determining the risk value of the behavior of the user comprises:
determining a baseline behavior rating based on the user login credentials;
calculating a behavior rating based on real time behavior data of a user during the digital reality session; and
comparing the baseline behavior rating and the calculated behavior rating.

13. A method for mitigating disorientation of a user transitioning from an augmented reality session to traditional reality, comprising:
monitoring the user's behavior during the augmented reality session;
in response to analyzing the user's behavior during the augmented reality session, generating a behavior risk rating associated with the user's behavior during the augmented reality session, the behavior risk rating indicates the danger of the user's behavior during the augmented reality session where a higher behavior risk rating is assigned to more dangerous behavior;
determining a behavior leakage risk associated with an end of the augmented reality session, the behavior leakage risk is the likelihood of the user continuing a certain behavior in traditional reality after being engaged in that behavior during the augmented reality session;
determining a leakage length based on the analyzed behavior associated with the user, the leakage length is a point in time during the augmented reality session the user would engage in similar activity as in the augmented reality session in the traditional reality without mitigation; and
in response to the leakage risk value being above a threshold value, modifying the augmented reality session.

14. The method of claim 13, further comprising:
recording the user's behavior prior to the user engaging in the augmented reality session; and
generating a baseline behavior history for the user.

15. The method of claim 13, further comprising:
periodically monitoring the behavior of the user after transitioning from the augmented reality session to traditional reality;
comparing the user's behavior after transitioning from the augmented reality session to traditional reality with the user's behavior during the augmented reality session;
in response to the comparison between the user's behavior after transitioning from the augmented reality session to traditional reality and the user's behavior during the augmented reality session generating and communicating a mitigation dialogue; and
in response to detecting a start user device session command, modify the user device session based on the generated modification of the user device session.

16. The method of claim 13, further comprising:
monitoring the user's behavior after transitioning from the augmented reality session to traditional reality; and
generating a mitigation dialogue based on the monitored behavior of the user after transitioning from the augmented reality session.

17. The method of claim 13, wherein monitoring the user's behavior during the augmented reality session comprises one or more of:
receiving a set of tactile data based on the user interaction with a user device;
receiving a set of body position data;
receiving geographical data associated with the user;
receiving social media data associated with the user; and
receiving a set of physiological sensor data associated with the user and above a predetermined threshold value.

18. The method of claim 13, wherein generating the behavior risk rating comprises:
   determining a baseline behavior rating based on the user login credentials;
   calculating a behavior rating based on real time behavior data of a user during the augmented reality session and
   comparing the baseline behavior rating and the calculated behavior rating.

19. The method of claim 13, wherein modifying the augmented reality session to prevent unwanted behavior from leaking and becoming actions taken by the user in traditional reality comprises one or more of:
   generating a text dialogue for display;
   generating an audio prompt associated with the generated dialogue for display;
   generating visual data for display; and
   communicating a hyperlink for display to the user device.

20. The method of claim 13, wherein the behavior leakage risk is further based on the nature of a simulation carried out during the augmented reality session and a user input device required to carry out that simulation.

* * * * *